United States Patent [19]
Wright

[11] Patent Number: 5,690,617
[45] Date of Patent: Nov. 25, 1997

[54] ADJUSTING CATHETER HOLDING DEVICE

[76] Inventor: Charles R. Wright, 3613 Singapore Cr., NE., Albuquerque, N. Mex. 87111

[21] Appl. No.: 745,658

[22] Filed: Nov. 8, 1996

Related U.S. Application Data

[60] Provisional application No. 60/006364, Nov. 8, 1995.
[51] Int. Cl.⁶ .................................................. A61M 5/32
[52] U.S. Cl. ........................... 604/179; 604/174; 604/178; 128/DIG. 26
[58] Field of Search .................................. 604/174, 178, 604/179, 180; 128/DIG. 26

[56] References Cited

U.S. PATENT DOCUMENTS

| | | | |
|---|---|---|---|
| 2,402,306 | 6/1946 | Turkel . | |
| 2,590,006 | 3/1952 | Gordon . | |
| 3,626,938 | 12/1971 | Versaci | 604/179 X |
| 3,957,082 | 5/1976 | Fuson et al. | 604/174 X |
| 4,360,025 | 11/1982 | Edwards | 604/180 |
| 4,453,933 | 6/1984 | Speaker | 604/179 |
| 4,585,443 | 4/1986 | Kaufman . | |
| 4,666,434 | 5/1987 | Kaufman | 604/179 |
| 5,069,206 | 12/1991 | Crosbie | 604/179 X |
| 5,084,026 | 1/1992 | Shapiro | 604/179 |
| 5,263,943 | 11/1993 | Vanderbrook | 604/179 X |
| 5,304,145 | 4/1994 | Blair | 604/179 |
| 5,529,062 | 6/1996 | Byrd | 604/179 X |
| 5,555,881 | 9/1996 | Rogers et al. | 604/179 X |

*Primary Examiner*—Sam Rimell
*Assistant Examiner*—Robert V. Racunas
*Attorney, Agent, or Firm*—DeWitt M. Morgan, Esq.; Kevin Lynn Wildenstein, Esq.

[57] ABSTRACT

The present invention discloses catheter tube retaining devices having a disk rotatably coupled to the base, and a strap (or equivalent) for attaching such a device to the human body. The disk is capable of rotation relative to the base through at least a 90 degree arc. Further, the disk has formed upon a top surface at least one U-shaped retaining channel or groove of sufficient diameter as to retain a catheter tube in interference fit, without restricting the passage of fluid through such tube. Preferably, at least one pair of opposing tabs (or equivalent) protrude over the retaining channel to assist in the retention of the catheter tube. The disk can accommodate four channels, for different sizes of catheter tubes.

10 Claims, 3 Drawing Sheets

ADJUSTING CATHETER HOLDING DEVICE

CROSS-REFERENCE TO RELATED APPLICATIONS

This is a continuation-in-part of provisional application 60/006364 filed Nov. 8, 1995.

BACKGROUND OF INVENTION

This invention relates to a device for attaching a portion of the tube or conduit portion of a catheter to the human body by use of a rotatable disk, which has at least one catheter tube retaining channel, attached to a base member.

Catheters are common devices employed in a variety of medical procedures. In general, catheters are defined as tubular medical devices for insertion into a canal, blood vessel, passageway or body cavity usually to permit the injection or withdrawal of fluids, to promote drainage, and/or to keep the passageway open. Some catheters include needle portions, others do not.

A portion of a conventional catheter 10 is seen in FIG. 1. One end of catheter 10 (not shown) which has one or more holes therein, is inserted into the human body while the other end of the catheter includes at least one tube opening 11 for drainage. Depending upon the medical procedure desired, catheter 10 may have one or more additional tube openings, such as illustrated at 13. In this configuration, tube opening 13 is used to inject a fluid (usually sterile water) into a conventional catheter balloon portion (not shown) for inflation of the balloon after the balloon has been inserted into a body cavity, such as a bladder. Tube opening 11 provides the pathway for withdrawal of body fluids, such as urine. Other tube openings (not shown) on catheter 10 can also be employed, such as to inject antibiotics for flushing out the body cavity or sterile fluid. Catheters of various diameter or sizes (e.g. 8, 10, 12, 14, 16, 18, 20, 22, 24, 26 and 28) are commonly used with adults.

Catheters are usually manufactured from latex, polyurethane or rubber, but can be manufactured from other materials. For example, silicon catheters are useful for extended medical treatments, while rigid catheters are made for insertion into small children and babies.

Because of their widespread use in varying medical procedures, several types of catheters exist which are manufactured for specialized medical procedures. For example, cardiac catheters include a flexible tube with a balloon-like tip that is threaded into a patient's coronary arteries during an angioplasty procedure and then inflated to flatten material that is clogging the arteries and obstructing blood flow. Similarly, catheters can also be used for alveolar lavage in respiratory disease therapy, while other types of catheters include, but are not limited to, rectal catheters, nasal catheters, epidural catheters and intravascular ultrasound (IVUS) catheters. Finally, catheters for urological or incontinence purpose (known as "foley" catheters) are also commonly known. There are several manufacturers of catheters, including Trek Medical of Tampa, Fla., Baxter Healthcare Corporation of McGaw Park, Ill., C. R. Bard of Covington, Gaz.. and Abbott Labs of North Chicago, Ill.

The term catheter is also applied to intravenous tubes ("IV tubes") which are typically used to permit the injection or withdrawal of fluids from the body. Similarly, several medical techniques incorporate electrical signal wire similar to a catheter's use, as such wires can be useful for stimulating (e.g., injecting) or monitoring (e.g., withdrawing) information from the human body.

After a catheter is inserted in the human body, the portion of the catheter which is external to the body is usually attached to the body at one or more locations. This is a recommended procedure for several reasons. First, because the catheter is usually directly coupled to a human cavity (e.g., such as a heart, vein or a bladder), any movement of the catheter near its entrance to the body may also result in movement of the catheter within the body. If the movement is continuous or repetitive, this will likely result in irritation to the body cavity and potentially result in infection. Second, several forms of catheters utilize a balloon to retain one end of the catheter in the body cavity.

As the catheter moves external to the body, the balloon similarly moves, resulting in friction between the tissue of the body cavity and the balloon. If this friction continues, the cavity tissue may begin to bleed. This is a common occurrence in urinary catheters, as blood frequently is found in urinary bags which are attached to a urinary catheter. It is believed that some, if not all, of this blood is the result of the friction between the catheter and the urinary tract/interior bladder surface.

Several methods exist for attaching the catheter to the body. For example, if the catheter is employed for incontinence or urological purposes, the catheter tube can be placed on men either on the inner or outer thigh through the use of adhesive tape, while in women, catheters are generally placed on the inner thigh. When attached to the human leg by adhesive tape, the catheter is initially snugly affixed between the leg and the adhesive tape. However, as a person continues to move in a natural manner, the tape adhesive loses its adhesion to the catheter, but generally remains adhesive to the human skin. In this situation, the catheter is no longer snugly fit between the tape and the skin, and begins to rub against the skin or body hair thereby irritating the skin. Naturally, this condition can be extremely painful to the patient, and can also result in infection if not properly treated, In other applications, the catheter portion extending from the body can also be attached to the body by means of a conventional rubber or Velcro strap. These types of straps are usually included with smaller incontinence bags which are used by patients with a urological catheter when traveling. While flexible, these types of straps are not effective at retaining the catheter in a stable position relative to body movement. For example, these straps, if not wrapped around the body properly, tend to slip off the body as it moves. Conversely, if the strap is too tight, it tends to irritate the skin whether or not the body moves, and could lead to infection of the skin. Further, if the strap is worn, old or contains a manufacturing defect, it could break, thereby allowing the catheter to freely swing without any retention to the body.

Finally, in some applications, catheters are purposely not attached to the body, but are allowed to freely swing. This is rarely a recommended procedure, as catheters such as IV tubes, can easily be displaced from the human body as it moves. Additionally, the freely swinging catheter can be unintentionally moved (such as during sleep) so as to result in extreme irritation and severe pain to the patient.

There are also well-known, severe problems associated with catheters' ripping out of patients when catheter tubes accidentally are caught on obstructions during patient transport causing injury and bleeding. Similarly, catheters can be ripped out, yanked out or otherwise cause injury when patients are walking and they step on the catheter tube.

Several other known problems exist in using catheters not related to their attachment to the body. For example, because catheters are typically constructed from pliable material, they tend to kink when bent beyond 45 degrees, thereby resulting in blockage of the catheter. When kinking occurs in urology catheters, fluid pressure within the bladder increases to the point that the fluid eventually seeps out of the human body resulting in an uncontrolled leakage. Further, this type of situation is likely to occur when a patient is asleep because as the patient normally moves throughout the night, the catheter similarly moves. If the catheter moves so as to bend beyond 45 degrees, it will likely block the fluid passage.

If catheter movement during normal body movement can be reduced and/or eliminated, it is believed that infection rates can be drastically reduced. Clearly, a need exists for retaining the external portion of the catheter in a stable position relative to the body during normal movement, to prevent irritation and pain from both the internal and external portions of the human body.

Catheter needle locating devices are disclosed in U.S. Pat. Nos. 4,585,443 and 4,666,434, both issued to J. M. Kaufman. Kaufman '443 discloses a device for securing catheter needles to grafts and the like implanted in patients, primarily for use in connection with dialysis treatment. The device includes an anchoring bracelet for attachment to the patient at a predetermined location at which the graft is located, and a rotatable saddle mounted in the anchoring bracelet, which saddle includes an aperture adapted to receive the needle portion of the catheter. The device also includes a contact surface having a shape adapted to mate with the graft, and a saddle channel extending between the aperture and the contact surface, so that the needle projects a predetermined distance from the contact surface when it has been inserted into the aperture, thereby permitting the needle to be accurately located in the graft and firmly anchored on the patient. In particular, when the device has been applied to the patient, as shown in FIG. 1 of Kaufman '443, the axis of rotation of the saddle will be perpendicular to the patient's skin. Thus, after application of the device to the patient, but prior to insertion of the needle, fine alignment between the needle and the graft can be affected by rotation of the saddle about its axis of rotation by a small degree. Similarly, Kaufman '434 discloses a device for securing catheter needles to grafts implanted in patients.

Accordingly, it is an object of the present invention to provide a catheter tube retaining device for use with a catheter tube, an IV tube, and electrical signal wires or like tubular structures, capable of retaining a portion of the tube or conduit portion of a catheter while simultaneously allowing rotational movement relative to the body as the body moves.

It is also an object of the present invention to provide a catheter tube retaining device having a base, a rotatable disk having at least one channel (or equivalent) for retaining a portion of the tube or conduit portion of a catheter and a pin attaching the base to the disk, to retain such portion of the catheter tube in a stable but rotatable position relative to the human body which results in minimal or no movement of the internal portion of the catheter.

It is a further object of the present invention to provide a catheter retaining device having a base and an attached rotatable disk having at least one channel (or equivalent) for retaining a portion of the tube or conduit portion of a catheter to prevent an external portion of such catheter tube from bending beyond a 45 degree angle, to thereby prevent tube kinking or blockage.

This invention improves both catheter use and safety, and further alleviates or reduces any patient irritation or pain associated with using a catheter.

SUMMARY OF INVENTION

A catheter tube holding device, including a base and a disk which includes structure for holding a length of catheter tubing. The device also includes structure to rotatably couple the disk to the base, whereby the disk, when it is holding a length of tubing, can rotate through (at least) a 90° arc, and a strap or other similar device for attaching the base to a human. Preferably, the structure for holding includes at least one longitudinal u-shaped groove in the disk, which has a diameter slightly smaller than the diameter of the length of tubing to be inserted therein. Also, preferably, the disk includes at least one pair of tabs or equivalent, which tabs are on opposite sides of and partially project over the longitudinal groove, to assist in holding the length of tubing in the longitudinal groove. The device may include at least one additional longitudinal u-shaped groove formed in the disk, in which case the diameter of the additional longitudinal groove is smaller than the diameter of the first longitudinal groove, whereby catheter tubes of different diameters can be accommodated. The additional longitudinal groove may be parallel to or at an angle to and intersecting the first longitudinal groove. The device may also include third and fourth longitudinal u-shaped grooves formed in the disk, two of the longitudinal grooves being parallel to each other and, simultaneously, perpendicular to the other two longitudinal grooves. In this last arrangement, the grooves accommodates catheter tube sizes 8–12, 14–18, 20–24, and 26–28. The diameter of the longitudinal grooves slightly compresses the length of tubing, without restricting the flow of fluid through such length of tubing.

DETAILED DESCRIPTION OF INVENTION

Figure 1:
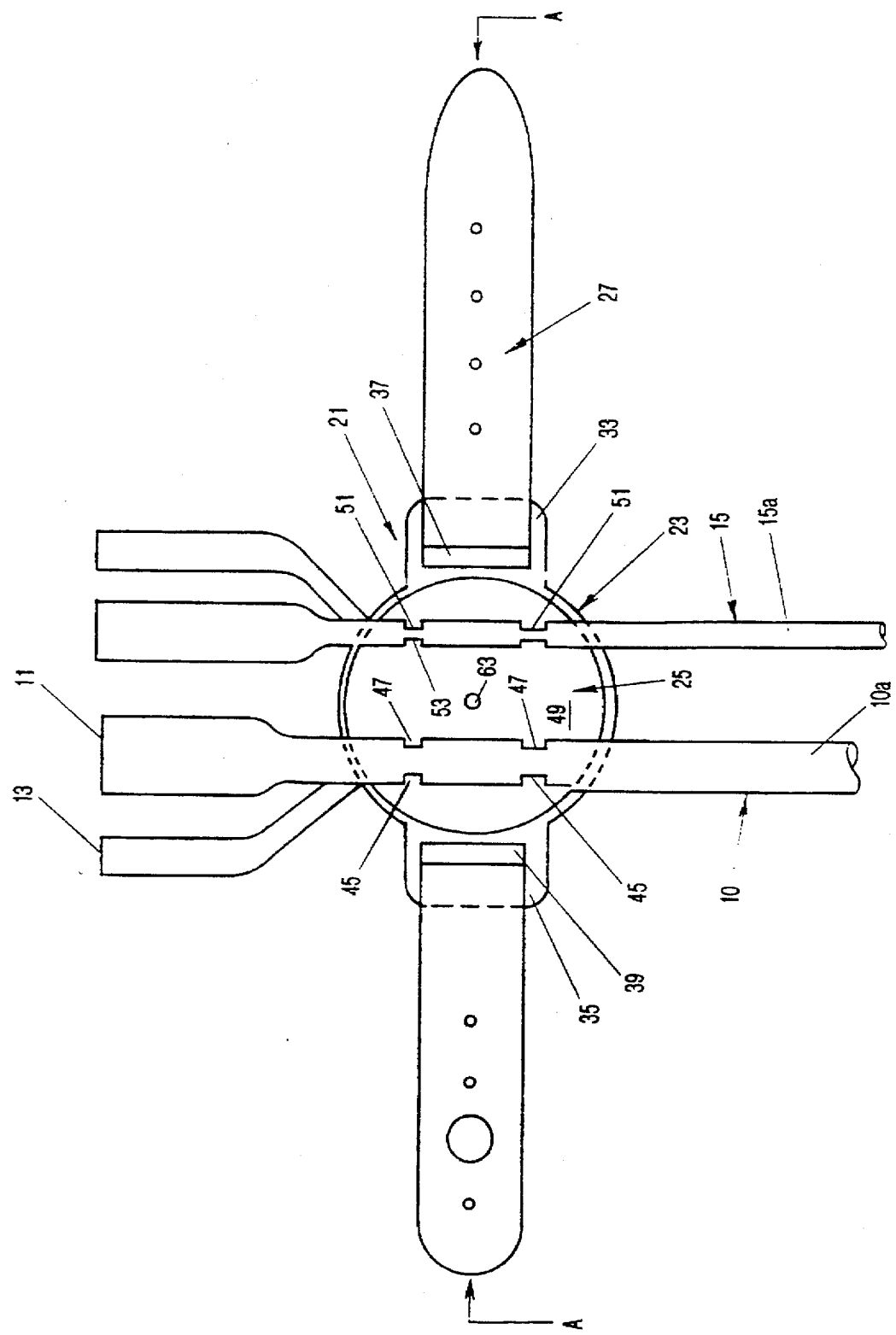
FIG. 1 is a top view of the first embodiment of the present invention.

As seen in FIG. 1, catheter retaining device 21 includes base 23, disk 25, and conventional strap 27 which is flexible and expandable in nature.

Figure 3:
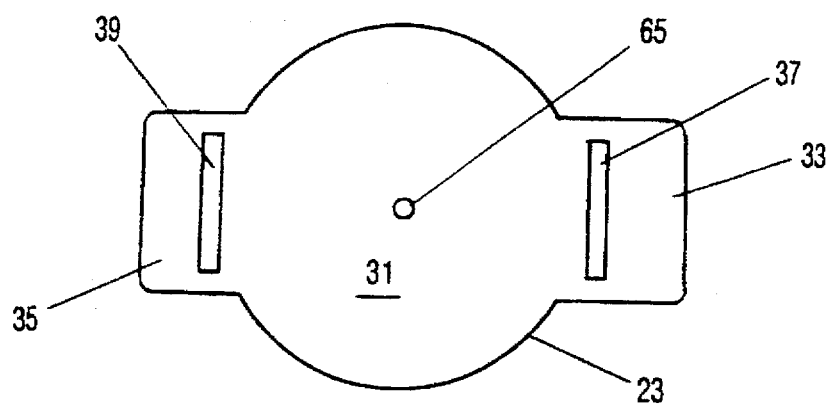
FIG. 3 is a top view of the base of the first embodiment.

As shown in FIG. 3, base 23 includes a center portion 31, having strap attachment portions 33 and 35 disposed on opposite sides thereof. While center portion 33 is of generally circular shape in the preferred embodiment, those skilled in the art will realize that the shape and size of base 23 is not critical as long as base 23 provides a solid, stable foundation for disk 25. Handle portions 33 and 35 extend outward from center portion 31 a short distance. Strap slots 37 and 39 formed within handle portions 33 and 35 respectively, are designed to receive and secure strap 27 to base 23.

Figure 2:
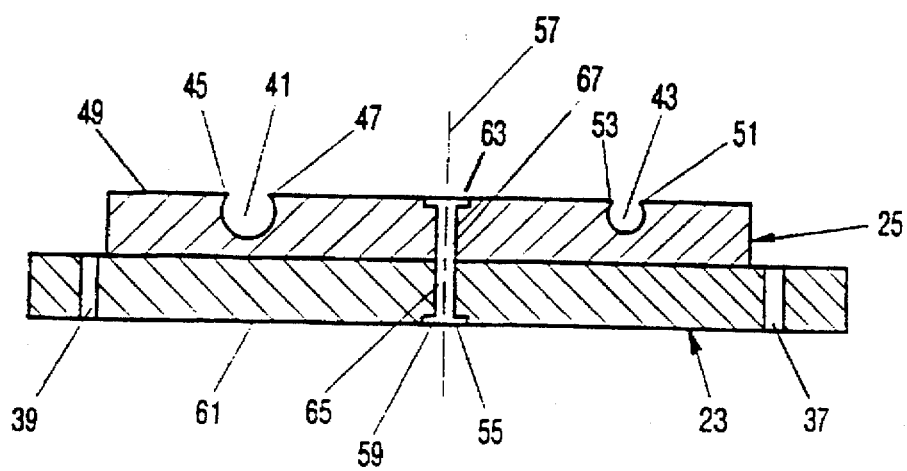
FIG. 2 is a side cross-sectional view of the first embodiment as shown along lines A—A in FIG. 1, without the detachable strap and catheter tubes.
Figure 4:
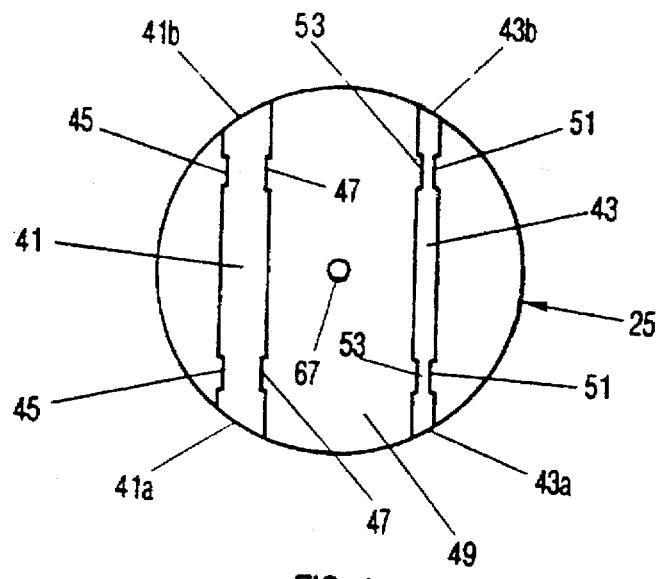
FIG. 4 is the top view of the disk of the first embodiment.

Similar to base 23, disk 25 is preferably circular in shape, but not necessarily limited to that particular geometry. At least one retaining channel 41 is longitudinally formed in disk 25. As illustrated in FIGS. 2 and 4, retaining channel 41 is generally formed as a U-shaped groove, and is formed at a sufficient depth and diameter as to retain a catheter tube (such as tube portion 10a) in an interference friction fit. The width of channel 41 should be sufficient to accommodate a range of sizes (e.g. 14–18, 20–24, etc.). As such, the diameter of retaining channel 41 should be slightly smaller than the diameter of the largest size catheter tube 10a to be retained. Additionally, those skilled in the art will appreciate that one or more additional U-shaped retaining channels, such as channel 43, can be formed in disk 25 for retaining a multitude of catheter tubes of another range of sizes (e.g., 8–12), such as indicated by tube portion 15a of catheter 15.

For channel 41, two pair of opposing tabs 45–47 are integrally formed upon and are flush with disk top surface 49 to assist in retaining the length of catheter tube 10a within retaining channel 41. Naturally, additional opposing tabs can be formed along the length of retaining channel 41. Opposing tabs 45–47 protrude over retaining channel 41 a short distance, but should not interfere with the quick insertion of and the quick release of catheter tubes as may be required during a medical emergency. Further, while tabs 45–47 can be formed in facing relation, they can also be offset throughout the length of retaining channel 41 as design considerations may require. Similarly, channel 43 is provided with two pair of opposing tabes 51–53, as illustrated in FIGS. 1, 2 and 4.

In another embodiment, not shown, U-shaped channel 41 can be replaced with retaining prongs having a U-shaped cross section upon top surface 49. In this fashion, cost savings and efficiency of space may be achieved as those skilled in the art will realize that a disk of narrower dimensions can be employed, while still achieving the novelty of the present invention.

Disk 25 is rotatably coupled to base 23 through any conventional coupling device which permits relative rotation of disk 25 to base 23, so long as such device does not interfere with or block the open ends (41a, 41b) of channel 41, or the open ends (43a, 43b) of channel 43, as disk 25 rotates relative to base 23. As seen in FIG. 2, coupling pin 55 allows disk 25 to rotate on a center axis relative to base 23. Pin 55, which is received in openings 65 and 67, is of sufficient length as to allow one end 59 to be flush with base bottom surface 61, and to allow another end 63 to be flush with top surface 49 of disk 25. Naturally, those of skill in the art will realize that coupling pin 55 can be integrally formed with base 23 for manufacturing convenience and potential cost savings. While disk 25 is capable of 360 degree rotation relative to base 23, due to the orientation of device 21 as it is attached to a patient, disk 25 is limited in normal use to a 90 degree rotational arc.

Base 23, disk 25 and pin 55 can be constructed of any lightweight, rigid material such as plastic suitable for hospital and patient use. In one embodiment, the bottom surface 61 of base 23 can be curved to follow the contour of the human body. Further, a soft material such as terry cloth, or an adhesive material can be applied to bottom surface 61 of base 23 as medical needs require. In this regard, a soft surface will prevent chafing and irritation of the skin, while an adhesive surface may be useful in situations where a strap is undesirable, such as when the patient is bathing.

In operation, catheter tube 10a is secured catheter retaining device 21 naturally forces disk 25 to rotate and swivel automatically relative to base 25 as the human body moves. The rotation of disk 25 is due to the natural inclination of a catheter tube to move as the human body moves.

Figure 5:
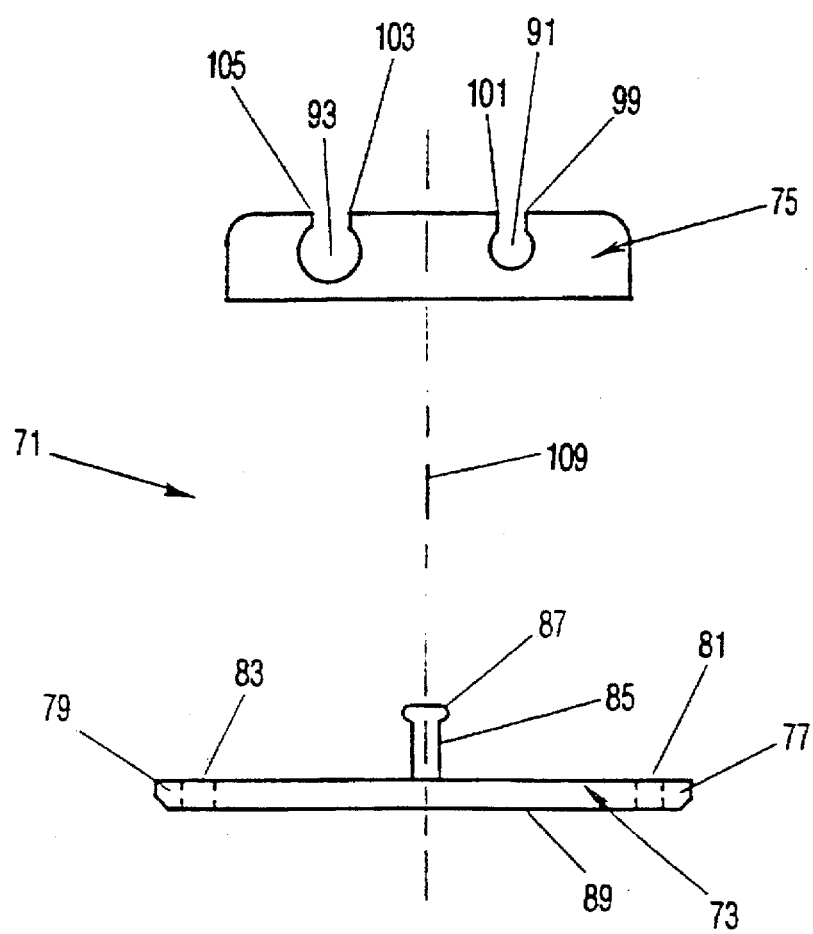
FIG. 5 is the exploded side view of the second embodiment of the invention.
Figure 6:
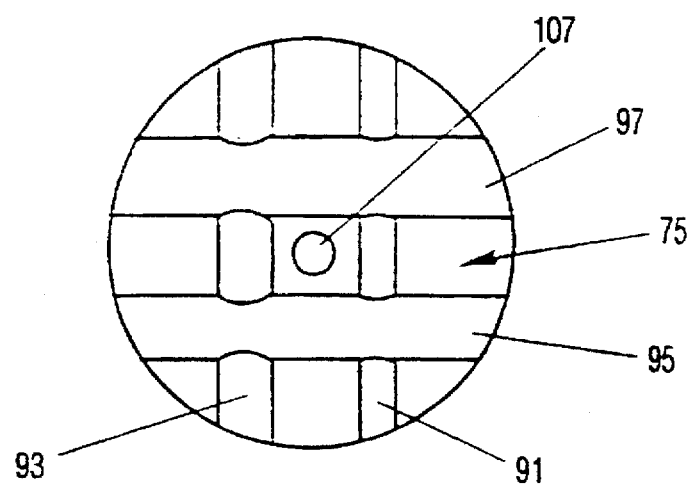
FIG. 6 is the top view of the disk portion of the embodiment of FIG. 5.

With reference to FIGS. 5 and 6, catheter retaining device 71 includes a base 73 and a rotatable disk 75. Base 73 has the same general shape as base 23, circular with handle portions 77 and 79 (which, in turn, include slots 81 and 83). Base 73, which is preferably molded of virgin polyurethane, includes an integral, central, upstanding post 85 with an enlarged head 87. The bottom 89 of base 73 also includes a longitudinal slot (not shown), interconnecting slots 81 and 83, to accommodate a strap (such as strap 27).

Disk 75, which is also preferably molded of virgin polyurethane, includes four channels 91, 93, 95 and 97. Channels 91 and 93 are parallel to each other and perpendicular to channels 95 and 97. As exemplified in FIG. 5, all four channels are U-shaped in cross-section, with the upper portions curved inward, to form lips, as indicated by 99, 101 and 103, 105, which extend the length of the associated channel. Disk 75 also includes a central aperture 107 which receives post 85, whereby disk 75 rotates relative to base 73 about axis 109. Aperture 107 includes a groove (not shown) which receives head 87 to hold the two parts in mating engagement.

As is evident from FIG. 6, the channels 91, 93, 95 and 97 are of progressively increasing width, to accommodate catheter tube sizes 8–12, 14–18, 20–24 and 26–28. Thus, for instance, the width of channel 91 is designed to be small enough to hold catheter tube sizes 8–12 with at least some friction, to prevent such tubes from moving longitudinally in channel 91. The surface of grooves 91, 93, 95 and 97 could be slightly roughed to further reduce the possibility of slipping.

Operation of retaining device 71 is the same as that of retaining device 21.

Whereas the drawings and accompanying description have shown and described the preferred embodiments of the present invention, it should be apparent to those skilled in the art that various changes may be made in the form of the invention without affecting the scope thereof.

I claim:

1. A catheter tube holding device, said device comprising:
   a. a base;
   b. a disk, said disk including means for holding a length of catheter tubing,
   c. means for rotatably coupling said disk to said base, whereby said disk, when holding said length of tubing, can rotate through, at least, a 90° arc; and
   d. means for removably attaching said base to a human.

2. The device according to claim 1, wherein said means for holding includes at least one longitudinal u-shaped groove in said disk.

3. The device according to claim 2, wherein said longitudinal groove has a diameter slightly smaller than the diameter of said length of tubing to be inserted therein.

4. The device according to claim 2, wherein said disk includes at least one pair of tabs, which tabs are on opposite sides of and partially project over said longitudinal groove, to assist in holding said length of tubing in said longitudinal groove.

5. The device according to claim 2, further including a second longitudinal u-shaped groove formed in said disk.

6. The device according to claim 5, wherein said second longitudinal groove has a diameter which is smaller than said diameter of said longitudinal groove, whereby catheter tubes of different diameters can be accommodated.

7. The device according to claim 5, wherein said second longitudinal groove is at an angle to and intersects said longitudinal groove.

8. The device according to claim 7, further including third and fourth longitudinal u-shaped grooves formed in said disk, two of said longitudinal grooves being parallel to each other and, simultaneously, perpendicular to the other two of said longitudinal grooves.

9. The device according to claim 8, wherein said longitudinal groove accommodates catheter tube sizes 8–12, said second longitudinal groove accommodates catheter tube sizes 14–18, said third longitudinal groove accommodates catheter tube sizes 20–24, said fourth longitudinal groove accommodates catheter tube sizes 26–28.

10. The device according to claim 3, wherein said diameter of said longitudinal groove slightly compresses said length of tubing, without restricting the flow of fluid through said length of tubing.

* * * * *

UNITED STATES PATENT AND TRADEMARK OFFICE
CERTIFICATE OF CORRECTION

PATENT NO. : 5,690,617

DATED : November 25, 1997

INVENTOR(S) : Charles R. Wright

It is certified that error appears in the above-identified patent and that said Letters Patent is hereby corrected as shown below:

Title page, under Related U.S. Application, should read –Provisional Application No. 60/006,365, filed November 8, 1995.

Signed and Sealed this

Second Day of March, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,690,617
DATED : November 25, 1997
INVENTOR(S) : Charles R. Wright It is certified that error appears in the above-identified patent and that said Letters Patent is hereby corrected as shown below:

Title page, under Related U.S. Application, should read –Provisional Application No. 60/006,365, filed November 8, 1996.--

This certificate supersedes Certificate of Correction issued March 2, 1999.

Signed and Sealed this

Twelfth Day of December, 2000

Attest:

Q. TODD DICKINSON

*Attesting Officer*    *Director of Patents and Trademarks*